United States Patent
Suzuki (10) Patent No.: US 12,419,594 B2
(45) Date of Patent: Sep. 23, 2025

(54) RADIOGRAPHING APPARATUS

(71) Applicant: CANON KABUSHIKI KAISHA, Tokyo (JP)

(72) Inventor: Masataka Suzuki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 412 days.

(21) Appl. No.: 18/058,478

(22) Filed: Nov. 23, 2022

(65) Prior Publication Data
US 2023/0172570 A1 Jun. 8, 2023

(30) Foreign Application Priority Data
Dec. 2, 2021 (JP) .................. 2021-196201

(51) Int. Cl.
*A61B 6/42* (2024.01)
*G03B 42/02* (2021.01)

(52) U.S. Cl.
CPC ............... *A61B 6/42* (2013.01); *G03B 42/02* (2013.01)

(58) Field of Classification Search
CPC ....... A61B 6/42; A61B 6/4233; A61B 6/4283; G03B 42/02; G03B 42/04
See application file for complete search history.

(56) References Cited

U.S. PATENT DOCUMENTS

| | | | |
|---|---|---|---|
| 2008/0078940 A1* | 4/2008 | Castleberry | G01T 1/20189 250/370.09 |
| 2017/0372572 A1* | 12/2017 | Kano | C22C 23/00 |
| 2020/0033377 A1* | 1/2020 | Kim | A61B 6/4283 |
| 2021/0041583 A1* | 2/2021 | Kralles | G01T 1/2006 |

FOREIGN PATENT DOCUMENTS

| | | |
|---|---|---|
| JP | 2008-129231 A | 6/2008 |
| JP | 2011-069740 A | 4/2011 |

* cited by examiner

*Primary Examiner* — David P Porta
*Assistant Examiner* — Mamadou Faye
(74) *Attorney, Agent, or Firm* — Canon U.S.A., Inc. IP Division

(57) ABSTRACT

A radiographing apparatus includes a support base and a housing. The support base includes a base side protruding portion that protrudes towards a bottom surface of the housing. The housing includes a housing side protruding portion that protrudes in a direction toward the support base. A first gap and a second gap are formed between the base side protruding portion and the housing side protruding portion in a perpendicular direction with respect to an incident direction of radiation at different positions. The first gap and the second gap are different from each other in distance in the perpendicular direction between the base side protruding portion and the housing side protruding portion.

10 Claims, 6 Drawing Sheets

RADIOGRAPHING APPARATUS

BACKGROUND

Field of the Disclosure

The present disclosure relates to a radiographing apparatus.

Description of the Related Art

A radiographing apparatus that detects intensity distribution of radiation having passed through an object and that acquires a radiographic image is publicly used at a site for non-destructive inspection for industrial purposes and a site for medical diagnosis. In order for such a radiographing apparatus to be able to achieve fast and wide-ranged imaging of a part, a thin, lightweight, portable imaging apparatuses, or so-called electronic cassettes, have been developed. However, there is a case where a user incautiously drops a highly portable radiographing apparatus.

Japanese Patent Application Laid-Open No. 2011-69740 discusses an X-ray image photographing apparatus having a support member on which a protruding portion is formed and a housing on which a recessed portion fitted to the protruding portion is formed. In the X-ray image photographing apparatus discussed in Japanese Patent Application Laid-Open No. 2011-69740, fitting of the protruding portion and the recessed portion to each other restrains movement of the support member in a direction perpendicular to an X-ray irradiation direction.

Japanese Patent Application Laid-Open No. 2008-129231 discusses a radiation image detector having a first engaging member arranged on a sensor supporting member, a second engaging member arranged on a back member, and a buffer material disposed between the first engaging member and the second engaging member. The radiation image detector discussed in Japanese Patent Application Laid-Open No. 2008-129231 exhibits shock resistance due to engagement of the first engaging member and the second engaging member with each other via the buffer material.

However, with a configuration discussed in Japanese Patent Application Laid-Open No. 2011-69740 or a configuration discussed in Japanese Patent Application Laid-Open No. 2008-129231, there may be a possibility that the protruding portion or the engaging members are broken, when an imaging apparatus drops and an impact is applied and transmitted to the protruding portion or the engaging members. In addition, if the housing, a support base, or the like is largely deformed when the imaging apparatus drops, there is a possibility that the fitting of the protruding portion and the recessed portion is released or an engagement relationship between the first engaging member and the second engaging member is lost. There is also an issue that the radiographing apparatus cannot be protected appropriately in such a case.

SUMMARY

Aspects of the present disclosure provide appropriate protection of a radiographing apparatus when an impact is applied to the radiographing apparatus.

A radiographing apparatus includes a radiation detector configured to detect radiation incident thereon in an incident direction, a support base configured to support the radiation detector, and a housing, containing the radiation detector and the support base, including an incident side with an incident surface on which the radiation is incident and a bottom side opposite to the incident side. The support base includes a base side protruding portion that protrudes in a direction toward the bottom surface from the support base. The housing includes a housing side protruding portion that protrudes in a direction toward the support base. A first gap and a second gap are formed between the base side protruding portion and the housing side protruding portion in a perpendicular direction with respect to the incident direction at different positions. The distance of the first gap and the distance of the second gap in the perpendicular direction between the base side protruding portion and the housing side protruding portion are different from each other.

Further features of the present disclosure will become apparent from the following description of exemplary embodiments with reference to the attached drawings.

DESCRIPTION OF THE EMBODIMENTS

Preferable exemplary embodiments of the present disclosure will be described below with reference to the accompanying drawings. Details of dimensions and configurations described in exemplary embodiments are not limited to those described in the exemplary embodiments and the drawings. Assume that radiation described in the exemplary embodiments includes, in addition to an X-ray, an α-ray, a β-ray, a γ-ray, a particle ray, and a cosmic ray.

Figure 1A:
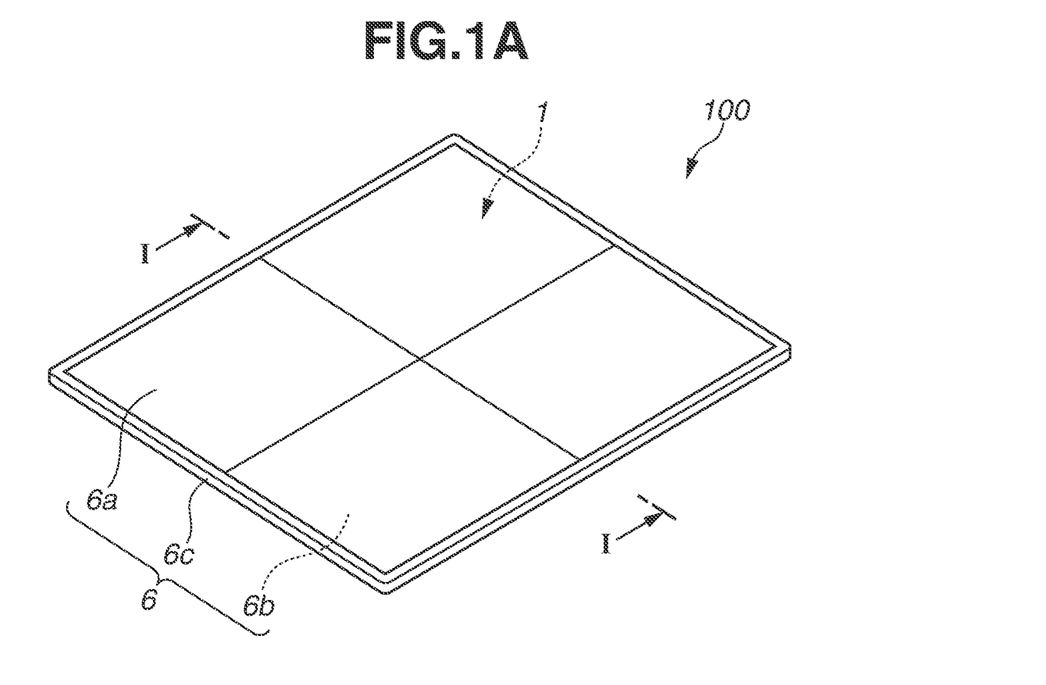
FIGS. 1A and 1B are perspective views each illustrating a configuration example of an outer appearance of a radiographing apparatus according to a first exemplary embodiment.
Figure 1B:
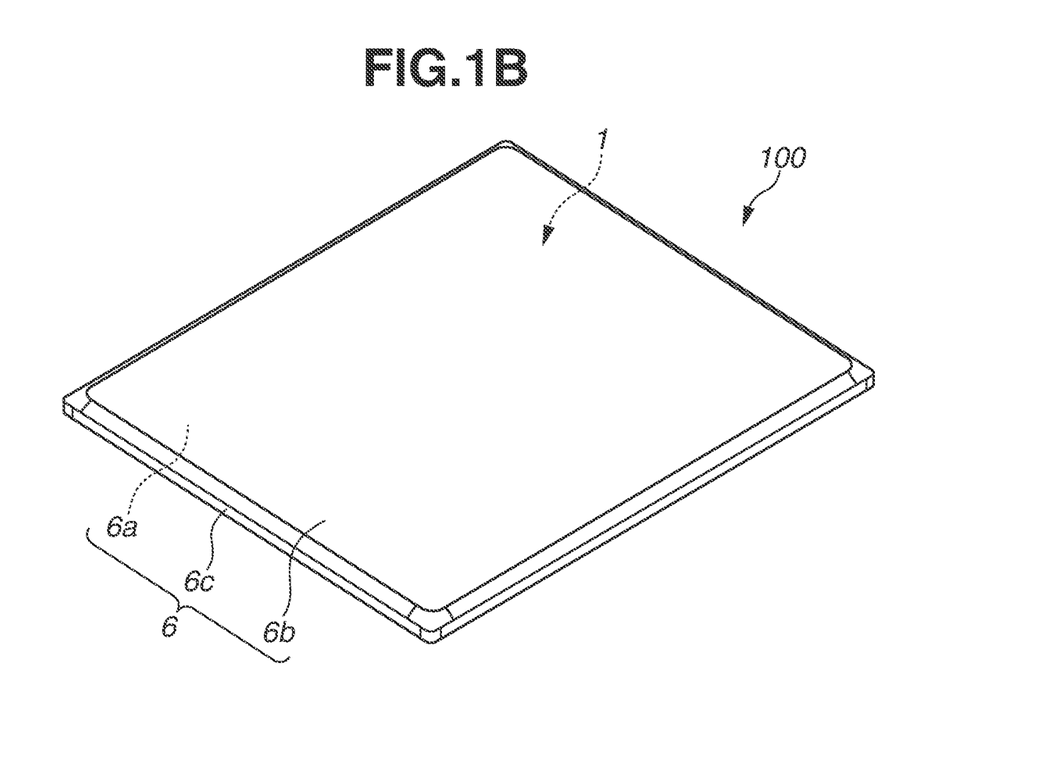

FIGS. 1A and 1B are perspective views each illustrating a configuration example of an outer appearance of a radiographing apparatus 100 according to a first exemplary embodiment. FIG. 1A is a diagram illustrating the radiographing apparatus 100 when viewed from an incident surface side. FIG. 1B is a diagram illustrating the radiographing apparatus 100 when viewed from a bottom surface side.

Figure 2A:
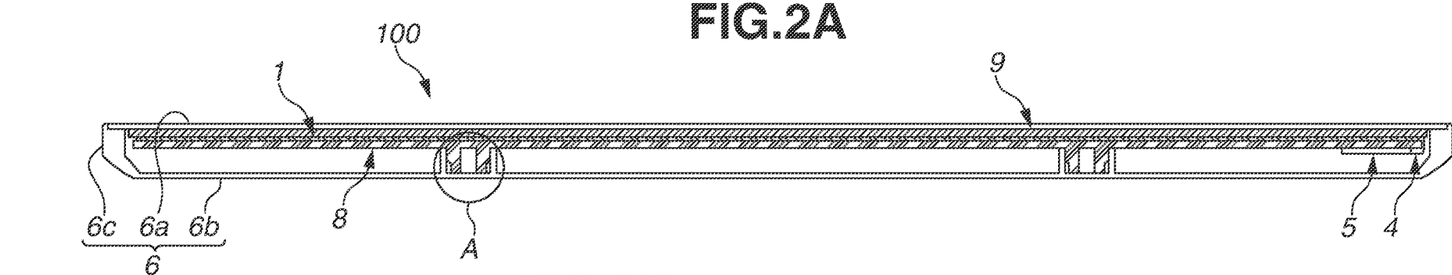
FIGS. 2A to 2C are diagrams each illustrating an internal configuration example of the radiographing apparatus.
Figure 2B:
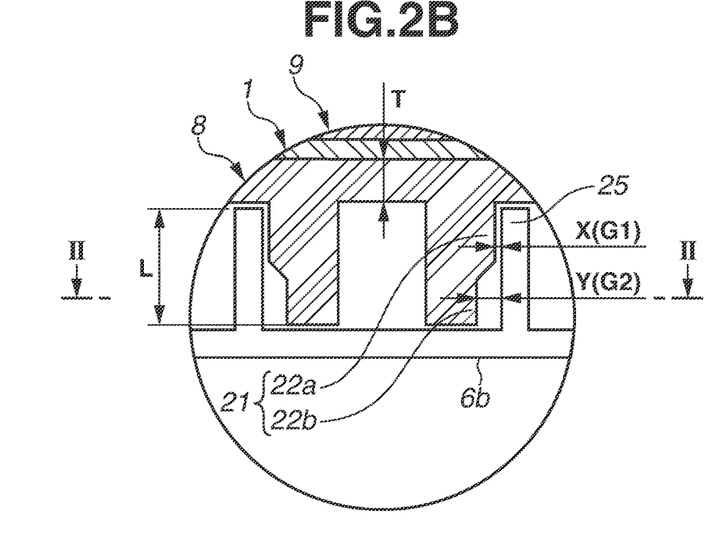
Figure 2C:
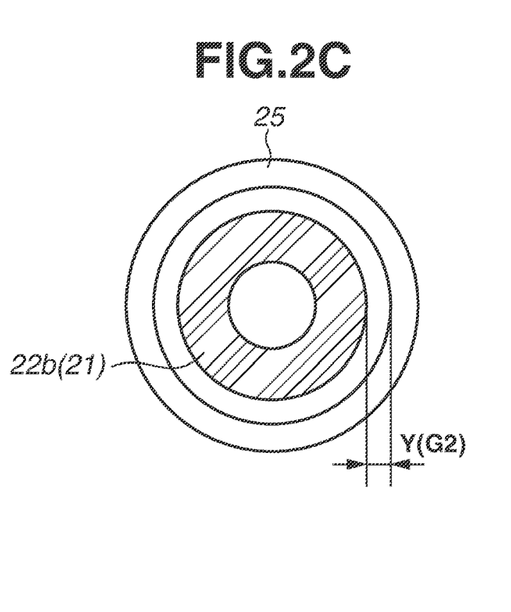

FIGS. 2A, 2B and 2C are diagrams each illustrating an internal configuration example of the radiographing apparatus 100. FIG. 2A is a cross-sectional view illustrating a cross section, which is obtained by cutting the radiographing apparatus 100 along I-I line in a direction in which radiation is incident (hereinafter referred to as an incident direction), when viewed from a direction of arrow. FIG. 2B is an enlarged view of an A-portion illustrated in FIG. 2A. FIG. 2C is a cross-sectional view along II-II line illustrated in FIG. 2B.

The radiographing apparatus 100 causes a radiation detection panel 1 serving as a radiation detector to detect radiation that has been emitted from a radiation generating apparatus and passed through an object. The radiographing apparatus 100 transfers an image detected by the radiation detection panel 1 to the outside, and the transferred image is displayed on an external monitor to be used for diagnosis or the like.

The radiation detection panel 1 is a panel of a so-called indirect conversion system, which is composed of, for example, a sensor substrate, on upper portion of which multitudes of photoelectric conversion elements (sensors) are disposed, a phosphor layer (scintillator layer) that is disposed on the sensor substrate, and a phosphor protective film. The radiation detection panel 1 may be a panel of a so-called direct conversion system, which is composed of a conversion element unit in which conversion elements made of amorphous selenium (a-Se) or the like and electric elements such as thin-film transistors (TFTs) are two-dimensionally disposed, and is not specifically limited.

The sensor substrate is formed of a material such as glass. However, the sensor substrate may be formed of a material, such as a resin with high flexibility, and is not specifically limited. The phosphor protective film protects a phosphor, and is formed of a material with low moisture permeability.

A control substrate 5 is connected to the radiation detection panel 1 via a flexible circuit board 4. The control substrate 5 reads out a detection signal from the radiation detection panel 1, and performs processing on the readout detection signal.

The radiographing apparatus 100 includes a housing (exterior package) 6 that houses therein the radiation detection panel 1, a support base 8 that supports the radiation detection panel 1, and an buffer material 9 that protects the radiation detection panel 1 from external force.

The housing 6 includes an incident surface 6a on which radiation is incident, a bottom surface 6b that is located opposite to the incident surface 6a, and a side surface 6c that connects the incident surface 6a and the bottom surface 6b. In the housing 6 according to the present exemplary embodiment, the bottom surface 6b and the side surface 6c are integrated with each other, and composed of one component. The component constituting the bottom surface 6b and the side surface 6c mentioned herein is referred to as a rear cover. The rear cover having a substantially bowl shape includes a standing wall at an outer edge thereof, and has a space that is open on the incident surface 6a side. The rear cover is formed of a material, such as an aluminum alloy, a magnesium alloy, a fiber reinforced resin, and a resin, each of which has an excellent lightweight property, but may be formed of another material. Meanwhile, the incident surface 6a is composed of one component. The component constituting the incident surface 6a mentioned herein is referred to as a front cover. The front cover is formed of a material, such as a carbon fiber reinforced resin, having high transmittance of radiation and an excellent lightweight property, but may be formed of another material. Two components of the rear cover and the front cover are fastened with screws, a gluing agent, an adhesive, or the like, whereby a space that allows the radiation detection panel 1 to be housed (contained) within the housing 6 is formed. The housing 6 preferably has a waterproof property.

The housing 6 of the present exemplary embodiment is composed of the two components, but may be composed of two or more components, and the number of components is not specifically limited. The housing 6 is divided between the incident surface 6a and the side surface 6c, but may be divided at any position. For example, the rear cover may be composed of two components by dividing the housing 6 between the side surface 6c and the bottom surface 6b. Alternatively, the side surface 6c itself may be divided between the incident surface 6a side and the bottom surface 6b side to integrally form the incident surface 6a side of the side surface 6c and the incident surface 6a. In this case, the front cover has a substantially bowl shape, similarly to the shape of the rear cover described above, and has a space that is open on the bottom surface 6b side.

The support base 8 supports the radiation detection panel 1 from the bottom surface 6b side. The support base 8 overlaps with the radiation detection panel 1 when viewed from the incident direction. The support base 8 is formed of a material, such as an aluminum alloy, a magnesium alloy, a fiber reinforced resin, and other resin, each of which has an excellent lightweight property, but may be formed of another material.

The buffer material 9 is disposed between the incident surface 6a and the radiation detection panel 1. The buffer material 9 is formed of a material, such as a foam resin and a gel, but may be formed of another material.

The radiographing apparatus 100 may include a battery for supplying necessary power. The battery may be a lithium-ion battery, an electric double layer capacitor, or an all-solid-state battery, but is not specifically limited. The radiographing apparatus 100 may include a display unit, such as a light emitting diode (LED), for displaying a state of the radiographing apparatus 100, a switch for an operator to give an instruction to the radiographing apparatus 100, a connector to and from which a wired connection cable for communicating with the outside is attached and detached, and an antenna for wireless communication.

Subsequently, a supporting structure of the radiographing apparatus 100 according to the present exemplary embodiment is described.

There is a case where the operator incautiously drops the radiographing apparatus 100 when performing image-capturing while handling the radiographing apparatus 100. Since an impact occurring at the time of the drop is applied to the radiographing apparatus 100, the radiographing apparatus 100, especially the radiation detection panel 1, needs to be protected appropriately when the impact is applied thereto.

The radiographing apparatus 100 according to the present exemplary embodiment has the supporting structure for appropriately protecting the radiographing apparatus 100 when the impact is applied thereto. Specifically, as illustrated in FIG. 2B, the support base 8 includes a base side protruding portion 21 that protrudes in a direction toward the bottom surface 6b (a bottom surface direction). The base side protruding portion 21 is formed integrally with the support base 8. Meanwhile, the housing 6 includes a housing side protruding portion 25 that protrudes in a direction from the bottom surface 6b side toward the support base 8 (an incident surface direction). The housing side protruding portion 25 is formed integrally with the rear cover of the housing 6. The front cover and the rear cover are brought close to each other along the incident direction for assembling of the housing 6, whereby the base side protruding portion 21 and the housing side protruding portion 25 are fitted to each other. The radiographing apparatus 100 has a configuration that, when an impact is applied to the radiographing apparatus 100, the base side protruding portion 21 and the housing side protruding portion 25 come in contact with each other, and thereby are subjected to the impact.

The base side protruding portion 21 and the housing side protruding portion 25 are further described.

An outer shape of the base side protruding portion 21 is substantially circular when viewed from the incident direction. Specifically, as illustrated in FIG. 2C, the base side protruding portion 21 has a substantially circular ring shape that allows the housing side protruding portion 25 to be fitted to the outside of the base side protruding portion 21.

An outer shape of the housing side protruding portion 25 is substantially circular and has a larger size than that of the base side protruding portion 21 when viewed from the incident direction. Specifically, as illustrated in FIG. 2C, the housing side protruding portion 25 has a substantially circular ring shape that allows the base side protruding portion 21 to be fitted to the inside of the housing side protruding portion 25.

The base side protruding portion 21 and the housing side protruding portion 25 are fitted to each other in a state where a gap is formed in a direction perpendicular to the incident direction (hereinafter referred to as the perpendicular direction). The gap between the base side protruding portion 21 and the housing side protruding portion 25 is a gap depending on a difference in dimension between an outer diameter of the base side protruding portion 21 and an inner diameter of the housing side protruding portion 25.

The gap is in a range that poses no problem in terms of usage even if the support base 8 moves in a plane direction inside the housing 6. The gap may be formed such that the base side protruding portion 21 and the housing side protruding portion 25 are partially in contact with each other, and is not specifically limited. When a state where the base side protruding portion 21 and the housing side protruding portion 25 are fitted to each other is viewed from the perpendicular direction, the base side protruding portion 21 and the housing side protruding portion 25 overlap with each other in a range of a length L along the incident direction, as illustrated in FIG. 2B. Assume that the length L is referred to as a fitting length.

The fitting length L is larger than a thickness T of the support base 8 in the incident direction.

The radiographing apparatus 100 is provided with a plurality of supporting structures each composed of the base side protruding portion 21 and the housing side protruding portion 25, and is capable of dispersing impact energy when an impact is applied to the radiographing apparatus 100.

In a case where the impact energy is large, it is assumed that stress is largely concentrated on the base side protruding portion 21 and the housing side protruding portion 25, and the base side protruding portion 21 and the housing side protruding portion 25 are broken. Especially, stress tends to be concentrated on the base side protruding portion 21, and stress is concentrated on a base end side of the base side protruding portion 21. This is because, when the impact is transmitted to the base side protruding portion 21, bending moment is applied thereto, and a load is applied to the base end side. Meanwhile, since deformation of the entire housing 6 enables dispersion of stress, the housing side protruding portion 25 tends to be less susceptible to stress concentration than the base side protruding portion 21. However, in a case where stiffness of the housing 6 or strength of a material is low, the housing side protruding portion 25 is more likely to be broken, and thus there is a case where stress concentration depends on a configuration of the radiographing apparatus 100.

There is also a case where the housing 6 instantly deforms at the time of dropping or use. When the rear cover deforms so as to bulge in a direction toward the bottom surface 6b, the base side protruding portion 21 and the housing side protruding portion 25 are separated from each other in the incident direction, and the fitting between the base side protruding portion 21 and the housing side protruding portion 25 is released. Increasing the fitting length L to prevent the fitting between the base side protruding portion 21 and the housing side protruding portion 25 from being released rather increases likelihood of stress concentration on the base side protruding portion 21.

The supporting structure according to the present exemplary embodiment is configured so as to prevent the fitting between the base side protruding portion 21 and the housing side protruding portion 25 from being released while mitigating stress concentration on the base side protruding portion 21. Specifically, a first gap G1 and a second gap G2 are formed at different positions between the base side protruding portion 21 and the housing side protruding portion 25. The first gap G1 and the second gap G2 are different from each other in distance in the perpendicular direction between the base side protruding portion 21 and the housing side protruding portion 25.

The base side protruding portion 21 has different outer diameters in the incident direction. Specifically, the base side protruding portion 21 has a large diameter portion 22a located on the base end side and a small diameter portion 22b located on a leading end side. The large diameter portion 22a and the small diameter portion 22b have substantially circular shapes whose centers coincide with each other when viewed from the incident direction. The large diameter portion 22a and the small diameter portion 22b are continuously connected via a taper. An outer diameter of the large diameter portion 22a is larger than an outer diameter of the small diameter portion 22b. That is, the outer diameter of the base side protruding portion 21 is large on the base end side and small on the leading end side. In contrast, the inner diameter of the housing side protruding portion 25 is substantially identical along the incident direction. Hence, in a state where the base side protruding portion 21 and the housing side protruding portion 25 are fitted to each other, a distance between the large diameter portion 22a of the base side protruding portion 21 and the housing side protruding portion 25 and a distance between the small diameter portion 22b of the base side protruding portion 21 and the housing side protruding portion 25 are different from each other.

The first gap G1 is a gap between the large diameter portion 22a of the base side protruding portion 21 and the housing side protruding portion 25. A distance X is a distance in the perpendicular direction between the large diameter portion 22a of the base side protruding portion 21 and the housing side protruding portion 25. The second gap G2 is a gap between the small diameter portion 22b of the base side protruding portion 21 and the housing side protruding portion 25. A distance Y is a distance in the perpendicular direction between the small diameter portion 22b of the base side protruding portion 21 and the housing side protruding portion 25. The distance X and the distance Y has a relationship in which the distance X is smaller than the distance Y (the distance X<the distance Y). The first gap G1 and the second gap G2 are separated from each other in the incident direction when viewed from the perpendicular direction. The first gap G1 is located on the incident surface 6a side, and the second gap G2 is located on the bottom surface 6b side.

In this manner, forming the first gap G1 and the second gap G2 having the relationship of the distance X<the distance Y between the base side protruding portion 21 and the housing side protruding portion 25 makes it harder to bring the leading end side of the base side protruding portion 21 into contact with the housing side protruding portion 25 when an impact is applied to the radiographing apparatus 100. That is, the base side protruding portion 21 and the housing side protruding portion 25 become harder to come in contact with each other in the second gap G2, whereby bending moment applied from the housing side protruding portion 25 to the base side protruding portion 21 becomes small when the impact is transmitted from the housing side protruding portion 25 to the base side protruding portion 21. This configuration can reduce stress concentration on the base side protruding portion 21, and can thereby prevent breakage of the base side protruding portion 21. In addition, the configuration can ensure the fitting length L between the base side protruding portion 21 and the housing side protruding portion 25, and can thereby prevent the fitting between the base side protruding portion 21 and the housing side protruding portion 25 from being released. Since the outer diameter of the base side protruding portion 21 is large on the base end side, the configuration can increase strength of a portion of the base side protruding portion 21 subjected to stress concentration.

As described above, the first gap G1 and the second gap G2 are formed at different positions between the base side protruding portion 21 and the housing side protruding portion 25, and are different from each other in distance in the perpendicular direction between the base side protruding portion 21 and the housing side protruding portion 25. The difference in distance in the perpendicular direction reduces the bending moment applied to the base side protruding portion 21 when an impact is applied to the radiographing apparatus 100.

Hence, the configuration mitigates stress concentration on the base side protruding portion 21 and can prevent breakage of the base side protruding portion 21, and can thereby protect the radiographing apparatus 100 appropriately. In addition, the configuration can prevent the fitting between the base side protruding portion 21 and the housing side protruding portion 25 from being released.

The description has been given of the case where the outer diameter of the base side protruding portion 21 is large on the base end side (incident surface 6a side), the outer diameter thereof is small on the leading end side (bottom surface 6b side), and the inner diameter of the housing side protruding portion 25 is substantially identical, but the configuration is not limited to this case. For example, in an opposite manner, the housing side protruding portion 25 may be configured such that the inner diameter thereof is large on the base end side (bottom surface 6b side), the inner diameter thereof is small on the leading end side (incident surface 6a side), and the outer diameter of the base side protruding portion 21 is substantially identical along the incident direction.

In the present exemplary embodiment, the description has been given of the case where the base side protruding portion 21 has the substantially circular ring shape and the housing side protruding portion 25 has the substantially circular ring shape, but the configuration is not limited to this case. At least one of the base side protruding portion 21 or the housing side protruding portion 25 may have a ring shape, part of which is missing, such as a substantially C-shape, when viewed from the incident direction. At least one of the base side protruding portion 21 or the housing side protruding portion 25 may have a shape other than the circular ring shape, such as a hexagonal shape and other polygons.

In the present exemplary embodiment, the description has been given of the case where the base side protruding portion 21 is formed integrally with the support base 8 and the housing side protruding portion 25 is formed integrally with the housing 6, but the configuration is not limited to this case. The base side protruding portion 21 may be a separate component aside from the support base 8 and the housing side protruding portion 25 may be a separate component aside from the housing side protruding portion 25. In a case of the separate component, the base side protruding portion 21 and the housing side protruding portion 25 are fastened or fitted to the support base 8 and the housing 6, respectively, and can thereby be formed integrally with the support base 8 and the housing 6, respectively. The base side protruding portion 21 and the housing side protruding portion 25 may be molded integrally with the support base 8 and the housing 6, respectively, from different materials into one component.

In a case where the housing 6 and the support base 8 are formed of conductive materials, a surface layer or the like of at least one of the base side protruding portion 21 or the housing side protruding portion 25 in contact with the other thereof can be formed of an insulating material, such as an insulating film and an insulating sheet, so that the housing 6 and the support base 8 are electrically insulated from each other.

Figure 3A:
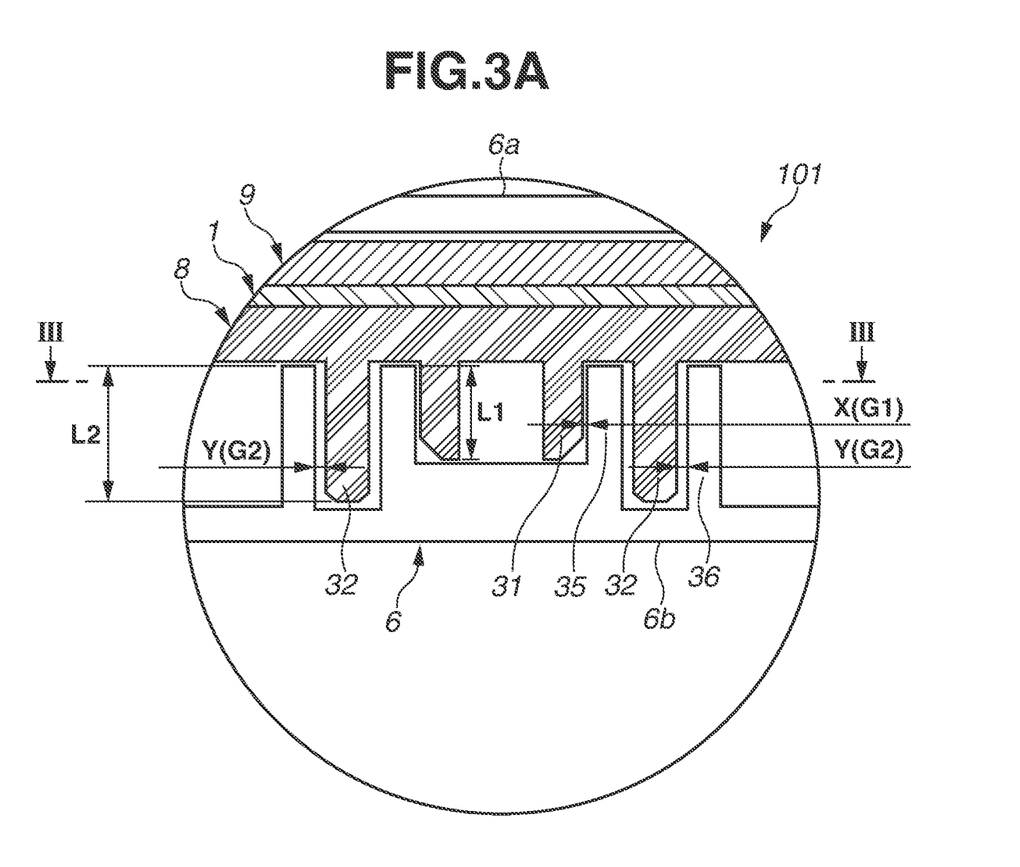
FIGS. 3A and 3B are diagrams each illustrating a configuration example of a radiographing apparatus according to a second exemplary embodiment.
Figure 3B:
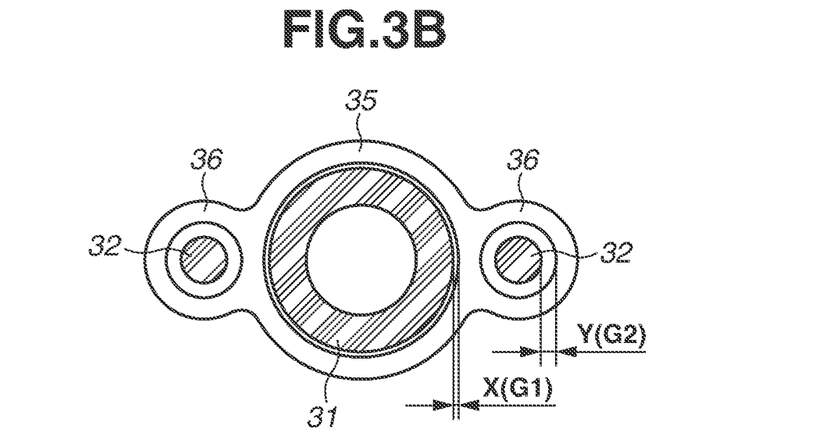

A radiographing apparatus 101 according to a second exemplary embodiment includes a plurality of base side protruding portions 31 and 32 having different shapes and a plurality of housing side protruding portions 35 and 36 having different shapes.

FIG. 3A is an enlarged view of a cross section of the radiographing apparatus 101. FIG. 3B is a cross-sectional view along III-III line illustrated in FIG. 3A. A part that is similar to that in the first exemplary embodiment is denoted by the same reference sign, and a description thereof is omitted.

As illustrated in FIG. 3A, the support base 8 includes two types of base side protruding portions 31 and 32 that protrude in a direction toward the bottom surface 6b. The present exemplary embodiment has a configuration including one base side protruding portion 31 and two base side protruding portions 32, which are separated from each other in the perpendicular direction. The base side protruding portion 31 and each of the base side protruding portions 32 have different shapes. Meanwhile, the housing 6 includes two types of housing side protruding portions 35 and 36 that protrude in a direction toward the support base 8. The present exemplary embodiment has a configuration including one housing side protruding portion 35 and two base side protruding portions 36, and the housing side protruding portion 35 and each of the two housing side protruding portions 36 are partially coupled to each other. The housing side protruding portion 35 and each of the housing side protruding portions 36 have different shapes.

An outer shape of the base side protruding portion 31 is substantially circular when viewed from the incident direction. Specifically, as illustrated in FIG. 3B, the base side protruding portion 31 has a substantially circular ring shape that allows the housing side protruding portion 35 to be fitted to the outside of the base side protruding portion 31. The base side protruding portion 31 is a part that is subjected to an impact when the radiographing apparatus 101 drops. An outer shape of the base side protruding portion 32 is substantially circular when viewed from the incident direction.

Specifically, as illustrated in FIG. 3B, the base side protruding portion 32 has a substantially columnar shape that allows the housing side protruding portion 36 to be fitted to the outside of the base side protruding portion 32. The base side protruding portion 32 is a part that prevents the fitting between the base side protruding portion 32 and the housing side protruding portion 36 from being released when an impact is applied to the radiographing apparatus 101 and the housing 6 is deformed.

The base side protruding portion 31 is located between the two base side protruding portions 32. In addition, an outer diameter of the base side protruding portion 31 is larger than an outer diameter of the base side protruding portion 32. A length of the base side protruding portion 31 from the support base 8 to the leading end is smaller than a length of the base side protruding portion 32 from the support base 8 to the leading end.

An outer shape of the housing side protruding portion 35 is substantially circular when viewed from the incident direction. Specifically, as illustrated in FIG. 3B, the housing side protruding portion 35 has a substantially circular ring shape that allows the base side protruding portion 31 to be fitted to the inside of the housing side protruding portion 35. An outer shape of the housing side protruding portion 36 is substantially circular when viewed from the incident direction. Specifically, as illustrated in FIG. 3B, the housing side protruding portion 36 has a substantially circular ring shape that allows the base side protruding portion 32 to be fitted to the inside of the housing side protruding portion 36.

The housing side protruding portion 35 is located between the two housing side protruding portions 36. An inner diameter of the housing side protruding portion 35 is larger than an inner diameter of the housing side protruding portion 36. A length of the housing side protruding portion 35 from the bottom surface 6b side to the leading end is substantially identical to a length of the housing side protruding portion 36 from the bottom surface 6b side to the leading end.

The base side protruding portions 31 and 32 and the housing side protruding portions 35 and 36 are fitted to each other, respectively, in a state where respective gaps are formed in the perpendicular direction. The gap between the base side protruding portion 31 and the housing side protruding portion 35 is a gap corresponding to a difference between the outer diameter of the base side protruding portion 31 and the inner diameter of the housing side protruding portion 35. The gap between the base side protruding portion 32 and the housing side protruding portion 36 is a gap corresponding to a difference between the outer diameter of the base side protruding portion 32 and the inner diameter of the housing side protruding portion 36. When a state where the base side protruding portions 31 and 32 and the housing side protruding portions 35 and 36 are fitted to each other, respectively, is viewed from the perpendicular direction, a fitting length L1 between the base side protruding portion 31 and the housing side protruding portion 35 is smaller than a fitting length L2 between the base side protruding portion 32 and the housing side protruding portion 36, as illustrated in FIG. 3A.

In the present exemplary embodiment, the first gap G1 is formed between the base side protruding portion 31 and the housing side protruding portion 35, and a distance therebetween in the perpendicular direction is a distance X. Meanwhile, the second gap G2 is formed between the base side protruding portion 32 and the housing side protruding portion 36, and a distance therebetween in the perpendicular direction is a distance Y. The distance X and the distance Y have a relationship in which the distance X is smaller than the distance Y (the distance X<the distance Y). That is, the first gap G1 between the base side protruding portion 31 and the housing side protruding portion 35 and the second gap G2 between the base side protruding portion 32 and the housing side protruding portion 36 are different from each other in distance in the perpendicular direction.

In this manner, the distance X of the first gap between the base side protruding portion 31 and the housing side protruding portion 35 that have the short fitting length L1 is made small and the distance Y of the second gap between the base side protruding portion 32 and the housing side protruding portion 36 that have the long fitting length L2 is made large. Hence, when an impact is applied to the radiographing apparatus 101, the base side protruding portion 31 in which the small gap (first gap G1) is formed is subjected to the impact, whereby the radiographing apparatus 101 is appropriately protected. In addition, the configuration can prevent the fitting between the base side protruding portion 32 and the housing side protruding portion 36 having the long fitting length (fitting length L2) from being released.

In the present exemplary embodiment, the description has been given of the case where the support base 8 has one base side protruding portion 31 and two base side protruding portions 32 and the housing 6 has one housing side protruding portion 35 and two housing side protruding portions 36, the configuration is not limited to this case. For example, the support base 8 is only required to have at least one base side protruding portion 31 and one base side protruding portion 32 and the housing 6 is only required to have at least one housing side protruding portion 35 and one housing side protruding portion 36, and the numbers thereof are not specifically limited.

Typically, there has been a demand for trimming weight of a radiographing apparatus for easier handling of the radiographing apparatus. However, a reduction in wall thickness of a housing for trimming weight makes the radiographing apparatus susceptible to deformation. To make a thickness of the radiographing apparatus in conformity with International Organization for Standardization (ISO) 4090:2001, there is a case where a sufficient fitting length between the base side protruding portion 21 and the housing side protruding portion 25 cannot be ensured. A radiographing apparatus 102 according to a third exemplary embodiment includes an intermediate member 10 between the base side protruding portion 21 and the housing side protruding portion 25, and thereby prevents the fitting between the base side protruding portion 21 and the housing side protruding portion 25 from being released even when the housing is susceptible to deformation.

Figure 4A:
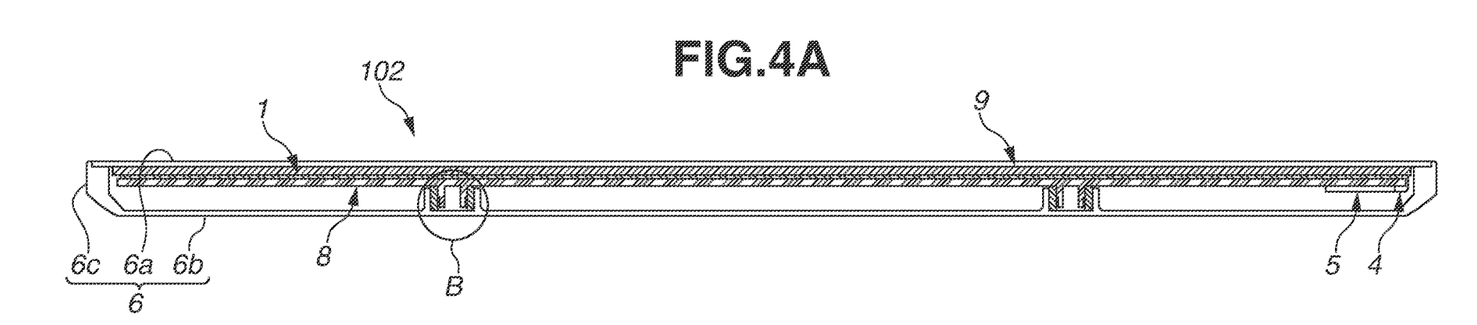
FIGS. 4A to 4C are diagrams each illustrating a configuration example of a radiographing apparatus according to a third exemplary embodiment.
Figure 4B:
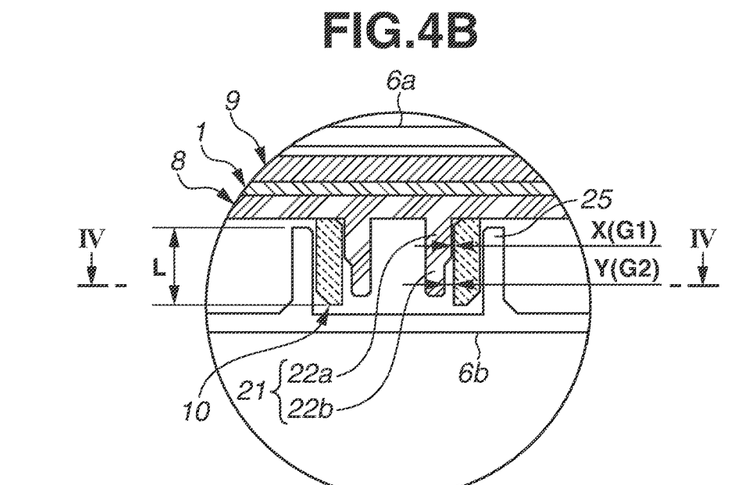
Figure 4C:
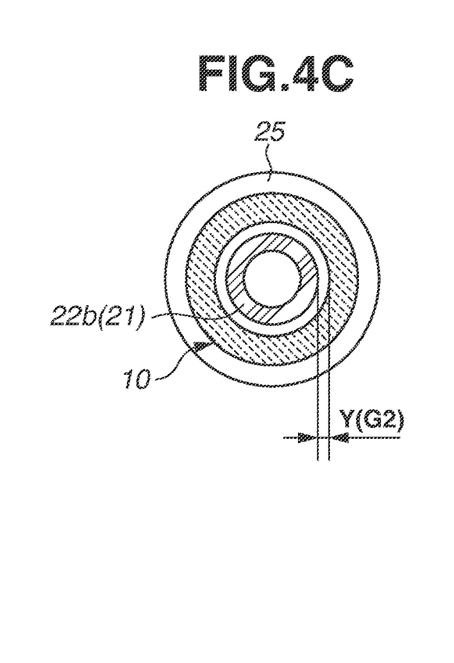

FIG. 4A is a cross-sectional view illustrating the radiographing apparatus 102. FIG. 4B is an enlarged view of a B-portion illustrated in FIG. 4A. FIG. 4C is a cross-sectional view along IV-IV line illustrated in FIG. 4B. A part that is similar to that in the first exemplary embodiment is denoted by the same reference sign, and a description thereof is omitted.

An outer shape of the intermediate member 10 is substantially circular when viewed from the incident direction. Specifically, as illustrated in FIG. 4C, the intermediate member 10 has a substantially circular ring shape, an inner diameter of the intermediate member 10 is substantially identical along the incident direction, and an outer diameter of the intermediate member 10 is substantially identical along the incident direction. The intermediate member 10 has such a shape as that allows the base side protruding portion 21 to be fitted to the inside of the intermediate member 10 and that allows the housing side protruding portion 25 to be fitted to the outside of the intermediate member 10.

The intermediate member 10 is formed of a material having an elastic modulus that is smaller than an elastic modulus of at least one of the base side protruding portion 21 or the housing side protruding portion 25. Specifically, the intermediate member 10 is formed of a resin material that has high impact strength and is hard to be crushed, such as polycarbonate, or a metal material, such as a magnesium alloy and an aluminum alloy. In a case where the housing 6 and the support base 8 are formed of conductive materials, the intermediate member 10 can be formed of an insulating material or a surface layer or the like of the intermediate member 10 in contact with the base side protruding portion 21 or the housing side protruding portion 25 can be formed of the insulating material so that the housing 6 and the support base 8 are electrically insulated from each other.

The intermediate member 10 is not fixed to the base side protruding portion 21 or the housing side protruding portion 25, and is movable along the incident direction. The intermediate member 10 is movable along the incident direction with some degree of friction with respect to the base side protruding portion 21 and the housing side protruding portion 25.

In the present exemplary embodiment, a first gap G1 and a second gap G2 are formed at different positions between the base side protruding portion 21 and the intermediate member 10. The first gap G1 and the second gap G2 are different from each other in distance in the perpendicular direction between the base side protruding portion 21 and the intermediate member 10.

The first gap G1 mentioned herein is a gap between the large diameter portion 22a of the base side protruding portion 21 and the intermediate member 10. A distance in the perpendicular direction between the large diameter portion 22a of the base side protruding portion 21 and the intermediate member 10 is a distance X. The second gap G2 is a gap between the small diameter portion 22b of the base side protruding portion 21 and the intermediate member 10. A distance in the perpendicular direction between the small diameter portion 22b of the base side protruding portion 21 and the intermediate member 10 is a distance Y. The distance X and the distance Y have the relationship in which the distance X is smaller than the distance Y (the distance X<the distance Y). The first gap G1 and the second gap G2 are separated from each other when viewed from the perpendicular direction.

In this manner, forming the first gap G1 and the second gap G2 having the relationship of the distance X<the distance Y between the base side protruding portion 21 and the intermediate member 10 reduces the bending moment applied from the housing side protruding portion 25 to the base side protruding portion 21 similarly to the first exemplary embodiment. This configuration can mitigate stress concentration applied on the base side protruding portion 21, and can thereby prevent breakage of the base side protruding portion 21.

Figure 5:
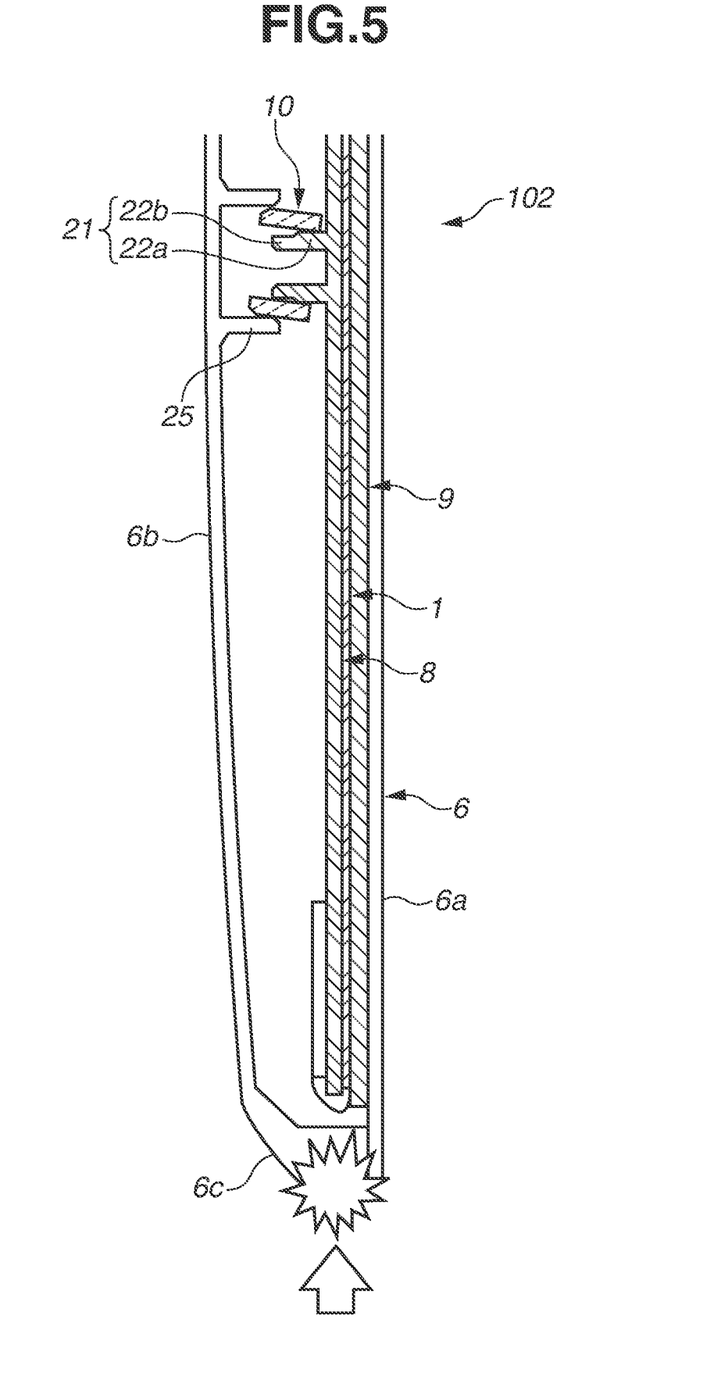
FIG. 5 is a diagram illustrating a state of an intermediate member when the radiographing apparatus drops.

FIG. 5 is a diagram illustrating a state of the intermediate member 10 when the radiographing apparatus 100 drops.

In FIG. 5, the radiographing apparatus 100 drops and collides with a floor surface, whereby an impact is applied to the housing 6. At this time, the intermediate member 10 is subjected to compressive force in the perpendicular direction between the base side protruding portion 21 and the housing side protruding portion 25, and thereafter the compressive force is mitigated. When an impact is applied to the housing 6, the housing 6 is deformed so as to expand in the incident direction. Especially, the rear cover having a bowl shape is subjected to a load from the side surface 6c and thereby tends to be deformed so as to bulge in the direction toward the bottom surface 6b because of bending moment. The support base 8 is not fixed in a thickness direction of the radiographing apparatus 102, and thus moves or deforms toward the incident surface 6a side of the housing 6. With the deformation of the rear cover and the movement or deformation of the support base 8, the base side protruding portion 21 and the housing side protruding portion 25 tend to move away from each other in the incident direction. Since friction occurs between the intermediate member 10 and each of the housing side protruding portion 25 and the base side protruding portion 21, the intermediate member 10 functions to prevent the base side protruding portion 21 and the housing side protruding portion 25 from being separated from each other in the incident direction.

As illustrated in FIG. 5, in a case where the base side protruding portion 21 and the housing side protruding portion 25 are separated from each other in the incident direction, the friction between the intermediate member 10 and the housing side protruding portion 25 causes the intermediate member 10 to move in a direction away from the support base 8, that is, toward the housing side protruding portion 25 side. At this time, the intermediate member 10 maintains a state of being fitted to each of the base side protruding portion 21 and the housing side protruding portion 25 while being somewhat inclined toward the support base 8. Specifically, the intermediate member 10 is in a state where the support base 8 side thereof is fitted to the base side protruding portion 21, and the bottom surface 6b side thereof is fitted to the housing side protruding portion 25. That is, even if the fitting length L between the base side protruding portion 21 and the housing side protruding portion 25 becomes small, or the base side protruding portion 21 and the housing side protruding portion 25 are separated from each other in the incident direction, the state between the base side protruding portion 21 and the housing side protruding portion 25 are fitted to each other via the intermediate member 10 is maintained. Hence, the intermediate member 10 can prevent the fitting between the base side protruding portion 21 and the housing side protruding portion 25 from being released.

In addition, since the intermediate member 10 is formed of, instead of an elastic body having flexibility such as rubber and a foam resin, a material having an elastic modulus that is smaller than an elastic modulus of a metallic material used for the base side protruding portion 21 and the housing side protruding portion 25 but is higher than an elastic modulus of the rubber or the foam resin, it is possible to prevent the intermediate member 10 from being largely deformed when an impact is applied to the housing 6. The intermediate member 10 is not largely deformed, whereby it is possible to prevent the base side protruding portion 21 and the housing side protruding portion 25 from being largely separated from each other in the incident direction. That is, the configuration can prevent the fitting between the base side protruding portion 21 and the housing side protruding portion 25 from being released. Additionally, the base side protruding portion 21 and the housing side protruding portion 25 are not largely separated from each other, whereby it is possible to prevent components from coming in contact with each other in the housing 6 and prevent breakage of a component due to an impact. The intermediate member 10 is not largely deformed, whereby it is possible to maintain the state where the leading end side of the base side protruding portion 21 is hard to come in contact with the housing side protruding portion 25 without reducing the distance Y of the second gap G2.

Supporting structures each composed of the base side protruding portion 21 and the housing side protruding portion 25 with the intermediate member 10 interposed therebetween may also be arranged at a plurality of locations. Arranging the supporting structures at the plurality of locations can prevent the fitting between the base side protruding portion 21 and the housing side protruding portion 25 from being released. Arranging the supporting structure according to the present exemplary embodiment in the perimeter that is close to the side surface 6c of the housing 6 when viewed from the incident direction can further prevent the fitting from being released. The impact force is transferred from the housing side protruding portion 25 to the base side protruding portion 21 via the intermediate member 10, whereby it is possible to mitigate stress concentration on the base side protruding portion 21 and reduce an amount of movement of the support base 8 in the plane direction.

In the present exemplary embodiment, the description has been given of the case where the inner diameter of the intermediate member 10 is substantially identical along the incident direction and the outer diameter of the intermediate member 10 is substantially identical along the incident direction, but the configuration is not limited to this case. For example, the inner diameter of the intermediate member 10 may be large on the bottom surface 6b side and small on the incident surface 6a side, and the outer diameter of the base side protruding portion 21 may be substantially identical along the incident direction.

The description has been given of the case where the intermediate member 10 has the substantially circular ring shape, but the configuration is not limited to this case. The intermediate member 10 may have, for example, a ring shape, part of which is missing, such as a substantially C-shape. The intermediate member 10 may also have a shape other than the circular ring shape, such as a hexagonal shape and other polygons.

Figure 6A:
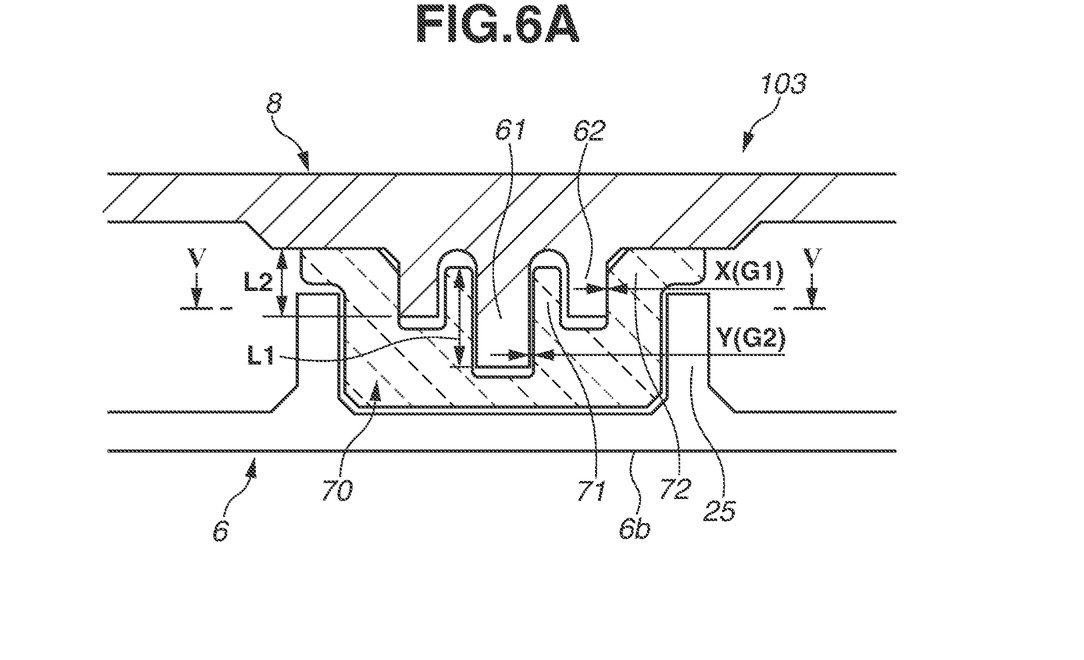
FIGS. 6A and 6B are diagrams each illustrating a configuration example of a radiographing apparatus according to a fourth exemplary embodiment.
Figure 6B:
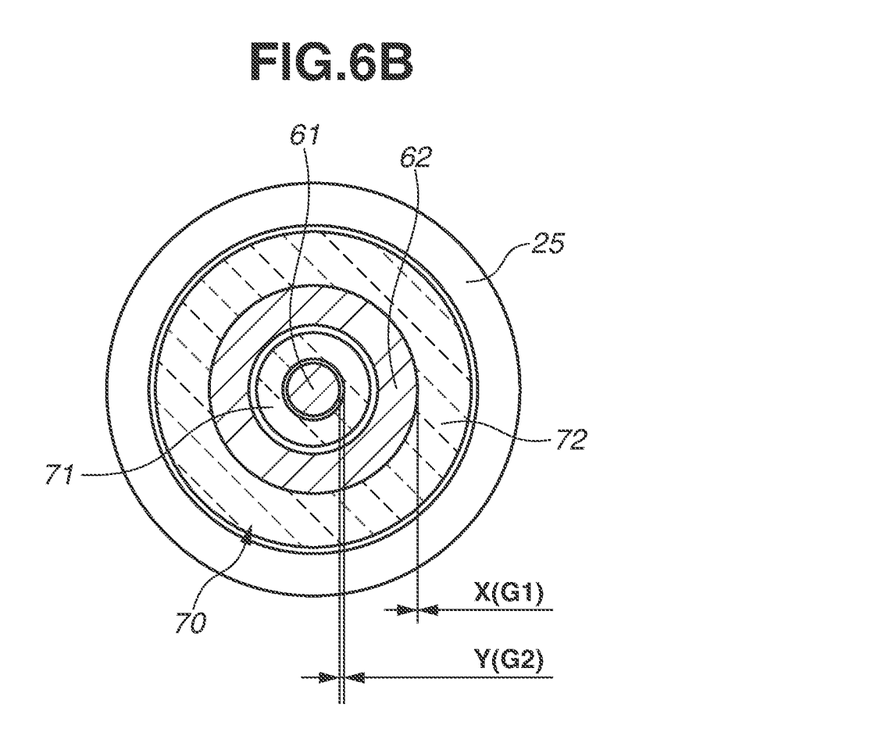

A radiographing apparatus 103 according to a fourth exemplary embodiment includes a plurality of base side protruding portions 61 and 62 having different shapes and an intermediate member 70 that conforms to shapes of the base side protruding portions 61 and 62.

FIG. 6A is an enlarged view of a cross section of the radiographing apparatus 103. FIG. 6B is a cross-sectional view along V-V line illustrated in FIG. 6A. A part that is similar to that in the first exemplary embodiment is denoted by the same reference sign, and a description thereof is omitted.

As illustrated in FIG. 6A, the support base 8 includes two types of base side protruding portion 61 and 62 that protrude in a direction toward the bottom surface 6b. The present exemplary embodiment has a configuration including one base side protruding portion 61 and one base side protruding portion 62. The base side protruding portion 61 and the base side protruding portion 62 have different shapes.

An outer shape of the base side protruding portion 61 is substantially circular when viewed from the incident direction. Specifically, as illustrated in FIG. 6B, the base side protruding portion 61 has a substantially columnar shape that allows a ring-shaped protruding portion 71 of an intermediate member 70 to be fitted to the outside of the base side protruding portion 61. The base side protruding portion 61 is a part that prevents the fitting between the base side protruding portion 61 and the ring-shaped protruding portion 71 from being released when the radiographing apparatus 103 is subjected to an impact and the housing 6 is deformed. An outer shape of the base side protruding portion 62 is substantially circular. Specifically, as illustrated in FIG. 6B, the base side protruding portion 62 has a substantially circular ring shape that allows the inside of a ring-shaped protruding portion 72 of the intermediate member 70 to be fitted to the outside of the base side protruding portion 62. The base side protruding portion 62 is a part that is subjected to an impact when the radiographing apparatus 103 drops.

The base side protruding portion 61 is located inside the base side protruding portion 62 so that the centers of the circles coincide with each other. An outer diameter of the base side protruding portion 62 is larger than an outer diameter of the base side protruding portion 61. A ring-shaped recessed portion that is recessed when viewed from the incident direction is formed between the base side protruding portion 61 and the base side protruding portion 62, and the ring-shaped protruding portion 71 is located in the recessed portion. A length of the base side protruding portion 61 from the support base 8 to the leading end is larger than a length of the base side protruding portion 62 from the support base 8 to the leading end.

As illustrated in FIG. 6A, the intermediate member 70 is located between the base side protruding portions 61 and 62 and the housing side protruding portion 25. The intermediate member 70 is formed of a material that is similar to that of the intermediate member 10 according to the third exemplary embodiment. The intermediate member 70 includes the two types of ring-shaped protruding portions 71 and 72 that protrude in a direction toward the support base 8. The present exemplary embodiment has a configuration including one ring-shaped protruding portion 71 and one ring-shaped protruding portion 72. The ring-shaped protruding portion 71 and the ring-shaped protruding portion 72 have different shapes.

An outer shape of the ring-shaped protruding portion 71 is substantially circular when viewed from the incident direction. Specifically, as illustrated in FIG. 6B, the ring-shaped protruding portion 71 has a substantially circular ring shape that allows the base side protruding portion 61 to be fitted to the inside of the ring-shaped protruding portion 71. An outer shape of the ring-shaped protruding portion 72 is substantially circular when viewed from the incident direction. Specifically, as illustrated in FIG. 6B, the ring-shaped protruding portion 72 has a substantially circular ring shape that allows the base side protruding portion 62 to be fitted to the inside of the ring-shaped protruding portion 72 and allows the housing side protruding portion 25 to be fitted to the outside of the ring-shaped protruding portion 72.

The ring-shaped protruding portion 71 is located inside the ring-shaped protruding portion 72 so that the centers of the circles coincide with each other. The base side protruding portion 61 is located inside the ring-shaped protruding portion 71, and a ring-shaped recessed portion that is recessed when viewed from the incident direction is formed between the ring-shaped protruding portion 71 and the ring-shaped protruding portion 72, and the base side protruding portion 62 is located in the recessed portion.

The base side protruding portion 61 and 62 and the ring-shaped protruding portions 71 and 72 are fitted to each other, respectively, in a state where respective gaps are formed in the perpendicular direction. The gap between the base side protruding portion 61 and the ring-shaped protruding portion 71 is a gap corresponding to a difference between the outer diameter of the base side protruding portion 61 and the inner diameter of the ring-shaped protruding portion 71. The gap between the base side protruding portion 62 and the ring-shaped protruding portion 72 is a gap corresponding to a difference between the outer diameter of the base side protruding portion 62 and the inner diameter of the ring-shaped protruding portion 72. When a state where the base side protruding portions 61 and 62 and the ring-shaped protruding portions 71 and 72 are fitted to each other, respectively, is viewed from the perpendicular direction, the fitting length L1 between the base side protruding portion 61 and the ring-shaped protruding portion 71 is larger than the fitting length L2 between the base side protruding portion 62 and the ring-shaped protruding portion 72.

In the present exemplary embodiment, a first gap G1 is formed between the base side protruding portion 62 and the ring-shaped protruding portion 72, and a distance therebetween in the perpendicular direction is a distance X. Meanwhile, a second gap G2 is formed between the base side protruding portion 61 and the ring-shaped protruding portion 71, and a distance therebetween in the perpendicular direction is a distance Y. The distance X and the distance Y have the relationship in which the distance X is smaller than the distance Y (the distance X<the distance Y).

Hence, in a case where an impact is applied to the radiographing apparatus 103, the base side protruding portion 62, in which the small gap (first gap G1) is formed, is subjected to the impact, whereby the radiographing apparatus 103 is appropriately protected. In addition, the configuration can prevent the fitting between the base side protruding portion 61 and the ring-shaped protruding portion 71 having the large fitting length (fitting length L1) from being released.

In this manner, the support base 8 includes the base side protruding portion 61 for preventing the fitting from being released and the base side protruding portion 62 for being subjected to an impact, and can thereby prevent breakage of the base side protruding portions 61 and 62 and also prevent the fitting from being released. Increasing the outer diameter of the base side protruding portion 62 for being subjected to the impact can mitigate stress concentration on the base side protruding portion 62. The intermediate member 70 is formed of the insulating material, whereby the housing 6 and the support base 8 can be insulated from each other.

While the description has been given of the present disclosure together with the various kinds of exemplary embodiments, the present disclosure is not limited only to these exemplary embodiments and can be modified and changed in various manners without departing from the scope of the present disclosure. For example, part of the configurations described in each of the exemplary embodiments can be combined with any of the other exemplary embodiments, or the modifications described in each of the exemplary embodiments can be applied to any of the other exemplary embodiments.

The present disclosure enables appropriate protection of the radiographing apparatus when an impact is applied to the radiographing apparatus.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from Japanese Patent Application No. 2021-196201, filed Dec. 2, 2021, which is hereby incorporated by reference herein in its entirety.

What is claimed is:

1. A radiographing apparatus comprising:
   a radiation detector configured to detect incident radiation;
   a support base configured to support the radiation detector; and
   a housing, containing the radiation detector and the support base, including an incident side with an incident surface on which the radiation is incident and a bottom side opposite to the incident side with a bottom surface,
   wherein the support base and the bottom surface are engaged with each other by an engagement portion in which a protruding portion provided to one thereof is inserted into a recessed portion provided to the other thereof, and
   wherein the protruding portion has, on a base side thereof, a contact surface that abuts the recessed portion in a direction orthogonal to an incident direction of the radiation when the protruding portion is in a state of no elastic deformation, and has, on a tip side thereof, a disengagement-preventing portion that is capable of abutting the recessed portion in the orthogonal direction when the protruding portion is in a state of elastic deformation.

2. The radiographing apparatus according to claim 1, wherein the protruding portion is formed on the support base, and the recessed portion is formed on the bottom surface of the housing.

3. The radiographing apparatus according to claim 2,
   wherein an outer shape of the protruding portion is substantially circular when viewed from the incident direction,
   wherein the recessed portion has a ring shape when viewed from the incident direction, the ring shape being a shape that allows the protruding portion to be fitted to inside of the recessed portion.

4. The radiographing apparatus according to claim 2, wherein the protruding portion extends from the support base toward the bottom surface in the incident direction, and includes a base end portion located closer to the support base, and a tip end portion located closer to the bottom surface,
   wherein, in the direction orthogonal to the incident direction, a first gap is formed between the base end portion and the recessed portion, and a second gap is formed between the tip end portion and the recessed portion, and
   wherein the first gap and the second gap are formed at respective positions separated from each other in the incident direction when viewed from a perpendicular direction with respect to the incident direction.

5. The radiographing apparatus according to claim 1, wherein a length of the first gap is smaller than a length of the second gap.

6. The radiographing apparatus according to claim 2, further comprising a plurality of protruding portions and a plurality of recessed portions.

7. The radiographing apparatus according to claim 6,
   wherein the support base includes the plurality of protruding portions and the housing includes the plurality of recessed portions,
   wherein the first gap is formed when a first protruding portion among the plurality of protruding portions and a first recessed portion among the plurality of recessed portions are fitted to each other, and
   wherein the second gap is formed when a second protruding portion among the plurality of protruding portions and a second recessed portion among the plurality of recessed portions are fitted to each other.

8. The radiographing apparatus according to claim 7,
   wherein an outer shape of the first protruding portion and an outer shape of the second protruding portion are different from each other when viewed from the incident direction, and wherein an outer shape of the first recessed portion and an outer shape of the second recessed portion are different from each other when viewed from the incident direction.

9. The radiographing apparatus according to claim 7, wherein a fitting length when the first protruding portion and the first recessed portion are fitted to each other is less than a fitting length when the second protruding portion and the second recessed portion are fitted to each other, and wherein a length of the first gap is smaller than a length of the second gap.

10. A radiographing apparatus comprising:

a radiation detector configured to detect radiation incident thereon in an incident direction;

a support base configured to support the radiation detector; and a housing, containing the radiation detector and the support base, including an incident side with an incident surface on which the radiation is incident and a bottom side opposite to the incident side with a bottom surface, wherein the support base and the bottom surface are engaged with each other by an engagement portion in which a protruding portion provided to one thereof is inserted into a recessed portion provided to the other thereof, wherein an intermediate member is arranged between the protruding portion and the recessed portion; and wherein the protruding portion has, on a base side thereof, a contact surface that abuts the intermediate member in a direction orthogonal to an incident direction of the radiation when the intermediate member is positioned such that an axis thereof is arranged along the incident direction, and wherein the protruding portion has, on a tip side thereof, a disengagement-preventing portion that is capable of abutting the intermediate member in the orthogonal direction when the intermediate member is positioned such that the axis thereof is tilted relative to the incident direction.

* * * * *